(12) United States Patent
Smith et al.

(10) Patent No.: US 6,548,261 B1
(45) Date of Patent: Apr. 15, 2003

(54) ALZHEIMER MODEL FOR DRUG SCREENING

(75) Inventors: Mark A. Smith, Cleveland, OH (US); Andrew McShea, Seattle, WA (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/223,588

(22) Filed: Dec. 30, 1998

(51) Int. Cl.$^7$ ................................................ G01N 33/53
(52) U.S. Cl. ........................ 435/7.1; 435/69.1; 435/325
(58) Field of Search ......................... 435/7.1, 325, 69.1

(56) References Cited

U.S. PATENT DOCUMENTS

| | | | |
|---|---|---|---|
| 5,134,062 A | 7/1992 | Blass | 435/7.21 |
| 5,221,607 A | 6/1993 | Cordell et al. | 435/6 |
| 5,547,841 A | 8/1996 | Marotta et al. | 435/6 |
| 5,720,936 A | 2/1998 | Wadsworth et al. | 424/9.1 |
| 5,994,084 A | * 11/1999 | Anderton et al. | |

OTHER PUBLICATIONS

Nuydens, R. et al., *Biochemical and Biophysical Research Communication*, 240(3):687.91, Nov. 1997.*

Arendt al., "Expression of the Cyclin–Dependent Kinase Inhibitor p16 in Alzheimer's Disease," *NeuroReport*, 7:3047–49 (1996).

Bentley and Groudine, "A block to elongation is largely responsible for decreased transcription of c–myc in differentiated HL60 cells," *Nature*, 321: 702–06 (1986).

Busser J et al., "Ectopic Cell Cycle Proteins Predict the Sites of Neuronal Cell Death in Alzheimer's Disease Brain," *J. Neurosicience*, 18(8):2801–807 (1998).

Caillet–Boudin and Delacorte, "Induction of a Specific Tau Alzheimer Epitope in SY–5Y Neuroblastoma Cells," *NeuroReport*, 8:307–10 (1996).

Chen, "The Alzheimer's Plaques, Tangles and Memory Deficits May Have a Common Origin; Part I; A Calcium Deficit Hypothesis," *Frontiers in Bioscience*, 2:a27–31 (1998).

Crowther, R. A., "Steps Towards a Mouse Model of Alzheimer's Disease," *BioEssays*, 17(7):593–95 (1995).

De Boni U, "Cultured Cells of the Nervous Systems, Including Human Neurones, in the Study of the Neuro–Degenerative Disorder, Alzheimer's Disease: An Overview," *Xenobiotica*, 15(8/9):643–47 (1985)

Evans D. A., et al., "Prevalence of Alzheimer's Disease in a Community Population of Older Persons," *JAMA*, 262(18):2551–556 (1989).

Farnsworth and L. Feig, "Dominant Inhibitory Mutations in the $Mg^{2+}$–Binding Site of $Ras^H$ Prevent its Activation by GTP," *Mol. Cell. Biol.*, 11:4822–4829 (1991).

Frautschy et al., "Rodent Models of Alzheimer's Disease: Rat Ab Infusion Approaches to Amyloid Deposits," *Neurobiol. of Aging*, 17(2):311–21 (1996).

Frederiksen et al., "Immortalized Neural cells From Trisomy 16 Mice as Models for Alzheimer's Disease," *Ann. NY Acad. Sci.*, 777:415–20 (1996).

Gartner et al., "Induction of $p21^{ras}$ in Alzheimer Pathology," *NeuroReport*, 6: 1313–316 (1995).

Hann et al., "Proteins Encoded by v–myc and c–myc Oncogenes: Indentification anad Localization Acute Leukemia Virus Transformants and Bursal Lymphoma Cell Lines," *Cell*, 34:789–98 (1983).

Jordon–Sciutto and R. Browser, "Alzheimer's Disease and Brian Development: Common Molecular Pathways," *Frontiers in Bioscience*, 3:d100–112 (1998).

Kuffler and Edwards J, "Mechanism of gamma aninobutyric acid (GABA) action and its relation to synaptic inhibition," *J. Neurophysiol.*, 21:589–610 (1965).

Leone et al., "Myc and Ras Collaborate in Inducing Accumulation of Active Cyclin E/Cdk2 and E2F," *Nature*, 387:422–426 (1997).

Mandekow EM and Mandelkow E, "Tau Protein and Alzheimer's Disease," *Neurobiol. of Aging*, 15(Suppl. 2):S85–86 (1994).

Maneiro et al., "Experimental Model to Study the Cytotoxic Effects Induced by β–Amyloid, Histamine, LPS and Serum from Alzheimer Patients on Cultured Rat Endothelial Cells," *Meth. Find. Exp. Clin. Pharmacol.*, 19(1):5–12 (1997).

McCoy et al, "Human Colon Carcinoma Ki–ras2 Oncogene and Its Corresponding Proto–Oncogene,"*Mol. Cell. Biol.*, 4:1577–1582 (1984).

McShea et al., "Re–entry Into the Cell Cycle: A Mechanism for Neurodegeneration in Alzheimer's Disease," *Med. Hypotheses*, 52(6);525–27 (1999).

McShea et al., "Mitotic Catastrophy in Alzheimer's Disease," *American Association of Neuropathologists Abstract*, (Jan., 1998).

McShea et al., "Abnormal Expression of the Cell Cycle Regulators P16 and CDK4 in Alzheimer's Disease," *Am. J. Pathol.*, 150(6): 1933–939 (1997).

Nagy et al., "Cell Cycle Markers in the Hippocampus in Alzheimer's Disease," *Acta Neuropathol (Berl)*, 94(1):6–15 (1997).

Neill et al., "Human IMR–32 Neuroblastoma Cells as a Model Cell Line in Alzheimer's Disease Research," *J Neurosci. Res.*, 39:482–93 (1994).

Nilsson et al., "The Essential Role of Inflammation and Induced Gene Expression in the Pathogenic Pathway of Alzheimer's Disease," *Frontiers in Bioscience*, 3: d436–446 (1998).

(List continued on next page.)

Primary Examiner—Marianne P. Allen
(74) Attorney, Agent, or Firm—Medlen & Carroll, LLP

(57) ABSTRACT

The present invention relates to methods and reagents for drug screening. Screening methods are disclosed employing neuronal cells that have been treated so as to exhibit characteristics associated with a re-entry into the cell cycle. One treatment approach comprises transfection of neuronal cells with an expression vector comprising one or more oncogenes.

6 Claims, 5 Drawing Sheets

OTHER PUBLICATIONS

Otuska et al., "Relaese of Gamma–Aminobutyric acid from inhibitory nerves of lobster,"*Proc. Natl. Acad. Sci. USA*, 56:1110–1115 (1966).

Price D.L. and S. S. Sisodia, "Mutant Genes in Familial Alzheimer's Disease and Transgenic Models," *Annu. Rev. Neurosci.*, 21:479–505. (1998).

Roses, A. D., "Apolipoprotein E Alleles as Risk Factors in alzheimer's Disease," *Annu. Rev. Med.*, 47:387–400 (1996).

Savory et al., "Reversal by Desferrioxamine of the Tau Protein Aggregates Following Two Days of Treatment in Aluminum–Induced Neurofibrillary Degeneration in Rabbit: Implications for Clinical Trials in Alzheimer's Disease," *NeuroToxicol.*, 19(2):209–14 (1998).

Usherwood and Grundfest, "Peripheral Inhibition in Skeletal Muscle of Insects," *J. Neurophysical.*, 28:497–518 (1965).

Vogel, "Tau Protein Mutations Confimed as Neuron Killers," *Science*, 280:1524–525 (1998).

Williams et al., "Apolipoprotein E Uptake and Low–Density Lipoprotein Receptor–Related Protein Expression by the NTera2/D1 Cell Line: A Cell Culture Model of Relevance for Late–Onset Alzheimer's Disease," *Neurobiol. of Disease*, 4:58–67 (1997).

Winters et al., "Cancer, Principles & Practice of Oncology," 3rd Ed., J.B. Lippincott Co., 59–60 (1989).

Yaar M, and B. A. Gilchrest, "Human Melanocytes as a Model System for Studies of Alzheimer's Disease," *Arch. Dermatol.*, 133:1287–291 (1997).

* cited by examiner

|            |     |     |     |     |     |     |     |     |     |     |
|------------|-----|-----|-----|-----|-----|-----|-----|-----|-----|-----|
| cKi-ras2-76 | 1<br>ATG | ACT | GAA | TAT | AAA | CTT | GTG | GTA | GTT | 10<br>GGA |
| cKi-ras2-76<br>SW-11-1 | 11<br>GCT | GGT<br>GTT | GGC | GTA | GGC | AAG | AGT | GCC | TTG | 20<br>ACG |
| cKi-ras2-76 | 21<br>ATA | CAG | CTA | ATT | CAG | AAT | CAT | TTT | GTG | 30<br>GAC |
| cKi-ras2-76 | 31<br>GAA | TAT | GAT | CCA | ACA | ATA | GAG | GAT | TCC | 40<br>TAC |
| cKi-ras2-76 | 41<br>AGG | AAG | CAA | GTA | GTA | ATT | GAT | GGA | GAA | 50<br>ACC |
| cKi-ras2-76 | 51<br>TGT | CTC | TTG | GAT | ATT | CTC | GAC | ACA | GCA | 60<br>GGT |
| cKi-ras2-76 | 61<br>CAA | GAG | GAG | TAC | AGT | GCA | ATG | AGG | GAC | 70<br>CAG |
| cKi-ras2-76 | 71<br>TAC | ATG | AGG | ACT | GGG | GAG | GGC | TTT | CTT | 80<br>TGT |
| cKi-ras2-76 | 81<br>GTA | TTT | GCC | ATA | AAT | AAT | ACT | AAA | TCA | 90<br>TTT |
| cKi-ras2-76 | 91<br>GAA | GAT | ATT | CAC | CAT | TAT | AGA | GAA | CAA | 100<br>ATT |
| cKi-ras2-76 | 101<br>AAA | AGA | GTT | AAG | GAC | TCT | GAA | GAT | GTA | 110<br>CCT |
| cKi-ras2-76 | 111<br>ATG | GTC | CTA | GTA | GGA | AAT | AAA | TGT | GAT | 120<br>TTG |
| cKi-ras2-76<br>SW-11-1 | 121<br>CCT | TCT<br>TCC | AGA | ACA | GTA | GAC | ACA | AAA | CAG | 130<br>GCT |
| cKi-ras2-76 | 131<br>CAG | GAC | TTA | GCA | AGA | AGT | TAT | GGA | ATT | 140<br>CCT |
| cKi-ras2-76 | 141<br>TTT | ATT | GAA | ACA | TCA | GCA | AAG | ACA | AGA | 150<br>CAG |
| cKi-ras2-76 | 151<br>GGT | GTT | GAT | GAT | GCC | TTC | TAT | ACA | TTA | 160<br>GTT |
| cKi-ras2-76 | 161<br>CGA | GAA | ATT | CGA | AAA | CAT | AAA | GAA | AAG | 170<br>ATG |
| cKi-ras2-76 | 171<br>AGC | AAA | GAT | GGT | AAA | AAG | AAG | AAA | AAG | 180<br>AAG |
| cKi-ras2-76 | 181<br>TCA | AAG | ACA | AAG | TGT | GTA | ATT | 188<br>ATG | TAA | |

Fig. 4

ALZHEIMER MODEL FOR DRUG SCREENING

FIELD OF THE INVENTION

The present invention relates to reagents and methods for drug screening, and more particularly, neuronal cells and tissue for screening potential Alzheimer therapeutics.

BACKGROUND

In 1907, Alois Alzheimer described the case of a 51-year-old woman with a rapidly degenerating memory who, after a swift deterioration, died severely demented four years later. This condition, which now bears Alzheimer's name, describes a fatal degenerative dementing disorder with initial mild memory impairment that progresses unrelentingly to a total debilitating loss of mental and physical faculties. Following symptom onset, the course of the disease varies considerably from a few years to over 20 years, with a mean survival of approximately 8 years. M. A. Smith, "Alzheimer Disease," *Internat. Rev. Neurobiol.* 42:1 (1998).

Alzheimer disease affects 10–15% of individuals over 65 years and up to 47% of individuals over the age of 80. In both clinical and autopsy series in the United States and Europe, Alzheimer disease accounts for approximately two-thirds of all dementias affecting elderly individuals. D. A. Evans et al., *J. Am. Med. Assoc.* 262: 2551 (1989).

The most common and distinctive lesions present with the diseased brain are the neuritic senile plaques and neurofibrillary tangles. The major protein component of senile plaque cores and vascular amyloid is a small polypeptide of approximately 4.2 kDa termed amyloid-$\beta$. A significant fraction of this protein is found to be associated with the cytoskeleton, presumably through its interaction with the microtubule-associated $\tau$ ("tau") protein. It is believed that the increased phosphorylated status of tau protein represents one of the earliest neuronal changes prior to the development of neurofibrillary tangles.

Unfortunately, because of the heterogeneity of the factors thought to be responsible for Alzheimer disease and the lack of an animal model displaying the full spectrum of pathological changes, successful pharmacological interventions have not been established. What is needed is an easy, reliable method to determine the safety and efficacy of candidate therapeutics for the treatment and/or prevention of Alzheimer disease.

Definitions

The term "drug" as used herein, refers to any medicinal substance used in humans or other animals. Encompassed within this definition are compound analogs, naturally occurring, synthetic and recombinant pharmaceuticals, hormones, neurotransmitters, etc. The present invention contemplates screening test compounds to identify a useful drug for the treatment of Alzheimers.

Most current attempts at therapeutics for Alzheimer disease are directed at neurotransmitter deficiencies. The term "neurotransmitter" includes any compound which functions in the nervous system to result in the transmission of chemical signals between cells. Examples of neurotransmitters include, but are not limited to neuropeptides, acetocholine, and amino acids (e.g., GABA). Other compounds are also contemplated, including dopamine, norepinephrine, etc.

The term "GABA" refers to $\gamma$-aminobutyric acid, a major inhibitory neurotransmitter in both vertebrates and invertebrates. Kuffler and Edwards, *J. Neurophysiol.*, 21:589 (1965; Otuska et al., *Proc. Natl. Acad. Sci USA* 56:1110 (1966); Usherwood and Grundfest, *J. Neurophysiol.*, 28:497 (1965). The term "GABA receptors" thus refers to structures expressed by cells and which recognize GABA.

The present invention contemplates the detection of a variety of therapeutic compounds, including but not limited to compounds that inhibit re-entry of neuronal cells into the cell cycle. Such compounds may be agonists or antagonists.

The term "agonist" refers to molecules or compounds which mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present.

The term "antagonist" refers to molecules or compounds which inhibit the action of a "native" or "natural" compound. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist. Or, antagonists may prevent the function of the agonist.

The term "host cell" or "cell" refers to any cell which is used in any of the screening assays of the present invention. The present invention contemplates "host cells" or "cells" in their natural states as well as genetically altered cells.

As used in the present invention, the term "transformation" refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector.

The term "gene" refers to a DNA sequence that comprises control and coding sequences necessary for the production of a polypeptide or precursor thereof. The polypeptide can be encoded by a full length coding sequence or by any portion of the coding sequence so long as the desired activity is retained. In the case of the present invention, oncogenes are contemplated and the desired activity is to cause neuronal cells and tissue to exhibit characteristics associated with re-entry into the cell cycle. Such characteristics may be cellular antigen expression (e.g. phospho-tau expression). On the other hand, a simple characteristic that can be readily measured is the incorporation of a nucleic acid precursor (indicating that the cells are traversing the S-phase of the cell cycle). Such precursors include, but are not limited to, 8-bromodeoxyuridine and tritiated-thymidine.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. The present invention contemplates wild-type oncogenes (e.g. from tumors) as well as oncogenes generated by mutation.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

SUMMARY OF THE INVENTION

The present invention relates to reagents and methods for drug screening, and more particularly, neuronal cells and tissue for screening potential Alzheimer therapeutics. It is not intended that the present invention be limited by the nature of the cells employed. In one embodiment, the cells are primary neurons. It is preferred that the cell employed is mammalian.

The present invention contemplates the use of neuronal cells treated in a manner such that they re-enter the cell cycle. The present invention contemplates using these treated cells in compound screening assays. The neuronal cells may be treated using chemical agents added to culture media. In a preferred embodiment, the neuronal cells are treated by transfecting them with an expression vector comprising one or more oncogenes (e.g. a combination of oncogenes).

In one embodiment, the present invention contemplates a neuronal cell (or cell culture) that has been subjected to treatment so as to exhibit at least one characteristic associated with the re-entry into the cell cycle. It is not intended that the present invention be limited by the nature of the treatment. However, in one embodiment, said treatment comprises transfection with an expression vector comprising one or more oncogenes. It is also not intended that the present invention be limited by the particular characteristic exhibited. However, in one embodiment, said characteristic comprises increased phosphorylation of the tau protein.

In one embodiment, the present invention contemplates a compound screening method comprising: a) providing, in any order: i) a reaction vessel; ii) a plurality of neuronal cells treated such that they exhibit at least one characteristic associated with the re-entry into the cell cycle; iii) a test compound b) combining said cells and said compound within said reaction vessel under conditions such that said compound is free to interact with said cells; and c) detecting said interaction. Again, it is not intended that the present invention be limited by the nature of the treatment. However, in one embodiment, said treatment comprises transfection with an expression vector comprising one or more oncogenes. It is also not intended that the present invention be limited by the particular characteristic exhibited. However, in one embodiment, said characteristic comprises expression of the tau protein.

It is not intended that the present invention be limited by the nature of the reaction vessel. Such screening can be done in a microwell of a microtiter plate. Alternatively, newer, high-throughput screening formats can be used (e.g. silicon-based systems). In one embodiment, the present invention also contemplates determining the viability of the cells after contact with the test compound.

DESCRIPTION OF THE DRAWINGS

FIG. 4 (SEQ ID NO:1 and SEQ ID NO:2) shows the nucleotide sequences of the coding regions of cDNAs corresponding to the Ki-ras2 proto-oncogene (cKI-ras2-76) and the Ki-ras2 transforming allele present in the human colon carcinoma cell line SW480 (SW-11-1).

DESCRIPTION OF THE INVENTION

The present invention relates to reagents and methods for drug screening, and more particularly, neuronal cells and tissue for screening potential Alzheimer therapeutics. The present invention contemplates the use of neuronal cells treated in a manner such that they re-enter the cell cycle. The present invention contemplates using these treated cells in compound screening assays. A variety of treatment methods can be used, as long as the treatment results in detectable characteristics associated with return to the cell cycle. A preferred treatment method comprises transfecting neuronal cells with an expression vector comprising the coding sequence of one or more oncogenes.

A. Rationale

Many features of neurons undergoing degenerative changes in Alzheimer disease resemble those of neurons in development that involve entry into the cell cycle. In earlier studies, the present inventors found that several markers of the cell cycle, including cyclin dependent kinases and their cognate inhibitors are increased in neurons in Alzheimer disease in comparison to control brain. A. McShea et al., "Abnormal Expression of the Cell Cycle Regulators P16 and CDK4 in Alzheimer's Disease," *Amer. J. Path.* 150:1933 (1997). While it may appear paradoxical that cell cycle abnormalities would be important in quiescent neurons, the evidence suggests there is inappropriate stimulation for neurons to re-enter the cell cycle. Indeed, increases in the levels of cyclin-dependent kinases are the key signal that triggers progression through the cell cycle. Such cell cycle-related events in post-mitotic senescent neurons appear to be deleterious and contribute to biochemical abnormalities such as hyper-phosphorylation of cytoskeletal proteins, apoptotic-like events and oxidative stress, i.e., the same biochemical abnormalities found in neurons in Alzheimer disease.

Figure 1:
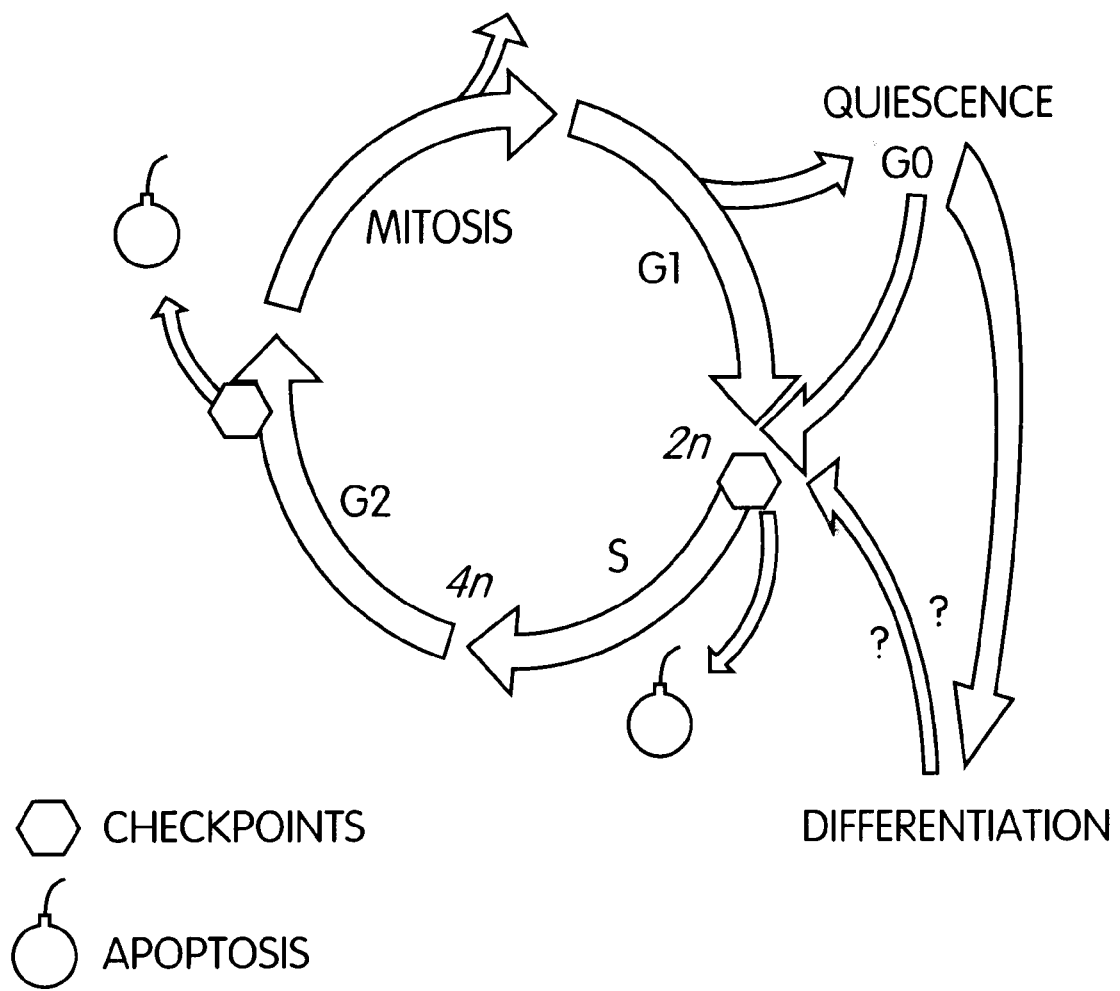
FIG. 1 is a schematic illustrating the re-entry into the cell cycle.

While the present invention is not limited by any theory or mechanism, as depicted in FIG. 1, it is believed that neuronal cells characteristic of Alzheimer disease have initiated by re-entry into the cell cycle. Although abortive exit from the cell division cycle can result in apoptosis, the continued presence of CDK inhibitors such as p16 and p21 indicate that the cell may not be initiating a mechanism used for programmed cell death but rather entering a dynamic state associated with senescence.

B. Treating Neuronal Cells

The present invention contemplates the use of neuronal cells treated in a manner such that they re-enter the cell cycle. The present invention contemplates using these treated cells in compound screening assays. The neuronal cells may be treated using chemical agents added to culture media. The present invention contemplates a method whereby agents are used to induce nucleotide incorporation in neuronal cells (e.g. primary neurons) with the purpose of producing a population of neuronal cells that have arrested just prior to mitosis and exhibit a phenotype similar to that observed in Alzheimer's disease In a preferred embodiment, the neuronal cells are treated by transfecting them with constructs comprising one or more oncogenes, thereby driving quiescent neuronal cells out of G0. It is not intended that the present invention be limited by the choice of the particular oncogene(s). A variety of oncogenes are contemplated, including but not limited to naturally occurring oncogenes and oncogenes generated by mutation.

Ras Genes. A variety of tumors and tumor cell lines contain mutated ras genes, which can be detected by their ability to induce foci of transformed cells upon transfection of FE monolayer cultures of NIH 3T3 mouse fibroblasts. Several of these activated ras genes have been cloned and found to arise by mutation of normal cellular proto-oncogenes. In some cases, the alterations responsible for the activation of these oncogenes are point mutations that affect the protein-encoding portions of these genes and change amino acid 12 or 61 of the 21-kilodalton ras protein ("p21"). The normal cellular Harvey sarcoma virus (Ha), Kirsten sarcoma virus (Ki), and N-ras proteins carry glycine as residue 12. Spontaneous mutations causing replacement of Gly 12 by a variety of residues, including valine, aspartic acid, or cysteine, have been shown to convert the human Harvey and Kirsten virus genes into active oncogenes. See e.g. M. McCoy et al., "Human Colon Carcinoma Ki-ras2 Oncogene and Its Corresponding Proto-Oncogene," *Mol. Cell. Biol.* 4:1577 (1984) (FIG. 4 of the present application was obtained from this reference).

Myc Genes. Myc is a nuclear proto-oncogene, and is the cellular counterpart to the oncogene v-myc carried by an acutely-transforming strain of the retrovirus avian leukosis virus. Myc is involved in the chromosome translocation t(8:13)(q24:q32) found in Burkitt's lymphoma where it is translocated into the immunoglobulin heavy chain gene. It encodes a transcription factor, forming a DNA-binding hetero-oligomer with the transcription factor Max. Several myc-related genes include c-myc, L-myc, and N-myc (Winters et al., Cancer, Principles & Practice of Oncology 3rd edition, pp. 59–60, J. B. Lippincott Company [1989]).

The c-myc gene product is a nuclear protein expressed in a wide variety of cell types, and has been implicated in the control of normal cell growth as well as transformation, but its exact function in unknown (Bentley and Groudine, Nature 321:

702–706 [1986]). The c-myc regions were initially defined by their homology with the transformation-specific segment (v-myc) of the avian defective acute leukemia virus MC29. In this virus, myc sequences interrupt and displace retroviral structural gene regions. This results in novel viral RNA and protein products composed of viral structural sequences covalently linked to v-myc (Hann et al., Cell 34: 789–798 [1983]). Examples of human myc oncogene GenBank accession numbers are M12026, M12027 and M16261.

Combinations Of Oncogenes. Data from the group of Nevins has demonstrated that certain combinations of oncogenes (Myc and Ras) can be used to drive quiescent fibroblasts out of G0, through G1, and into S-phase. Leone et al., "Myc and Ras collaborate in inducing accumulation of active cyclin E/Cdk2 and E2F" *Nature* 387:422 (1997). The present invention contemplates using such combinations of oncogenes to induce cell-cycle changes in neuronal cells and tissue. In one embodiment, the present inventors have adapted the adenovirus vector delivery system to induce high level expression of a constitutively active form of ras and wild-type c-myc into neuronal cells, such as primary neuronal cultures (described in the experimental section below). This transfection is adequate to induce alterations in cytoskeletal phosphorylation in adult neurons akin to that that occurs in Alzheimer disease. Thus, the present invention provides an in vitro model of the diseased brain which readily permits drug screening.

Other approaches. The present invention also contemplates other approaches to achieve the above-described effect. Other approaches similar to viral ras stimulation include constitutively active forms of: MAP kinase. Son-of-sevenless 1, GRB2, SHC, growth factor receptors including the TRK and NGF families. Alteratives to myc that are contemplated include mutants of mad and max.

The present invention also contemplates approaches involving transcription factor overexpression, e.g. E2F family member overexpression, modulation of retinoblastoma gene expression (e.g. by viral gene products), overexpression of cyclin dependent kinase family members or expression of cyclin dependent kinase inhibitor motifs to promote re-entry into the cell cycle by permitting reactivation of kinase activity pertaining to cell cycle control.

C. Detecting Re-Entry Into The Cell Cycle

Figure 2:
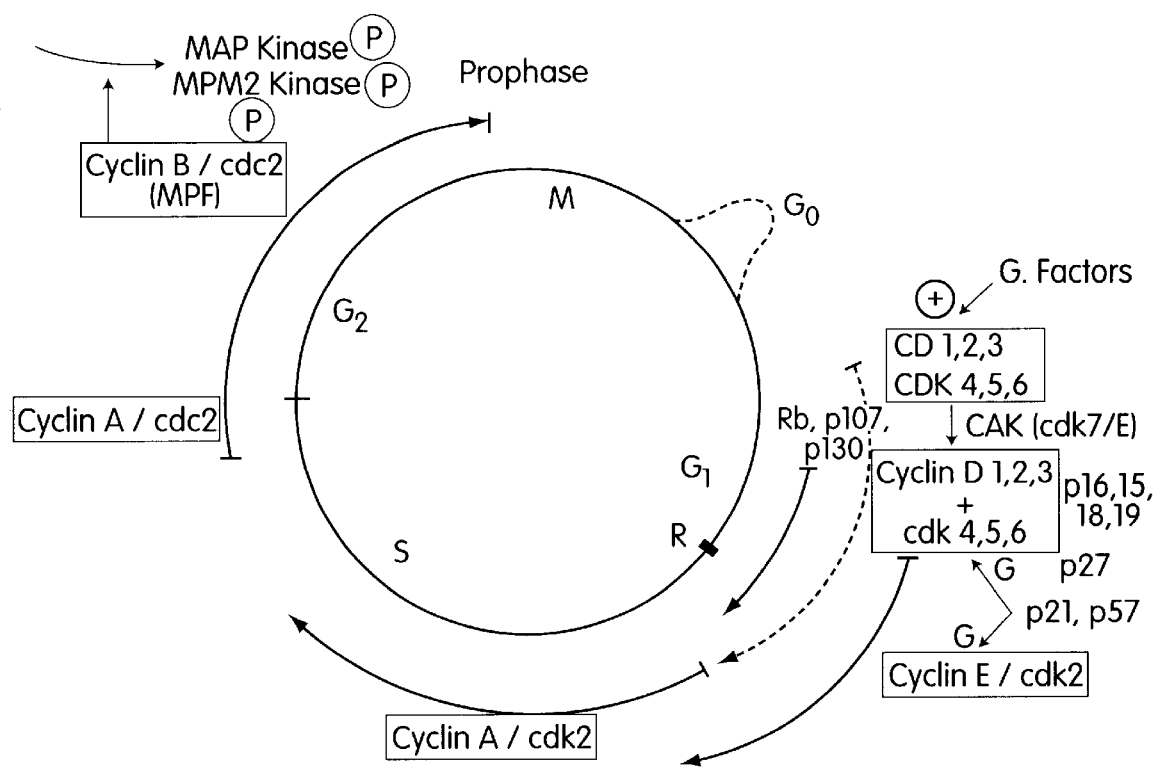
FIG. 2 is a schematic illustrating the control over the cell cycle.
Figure 3:
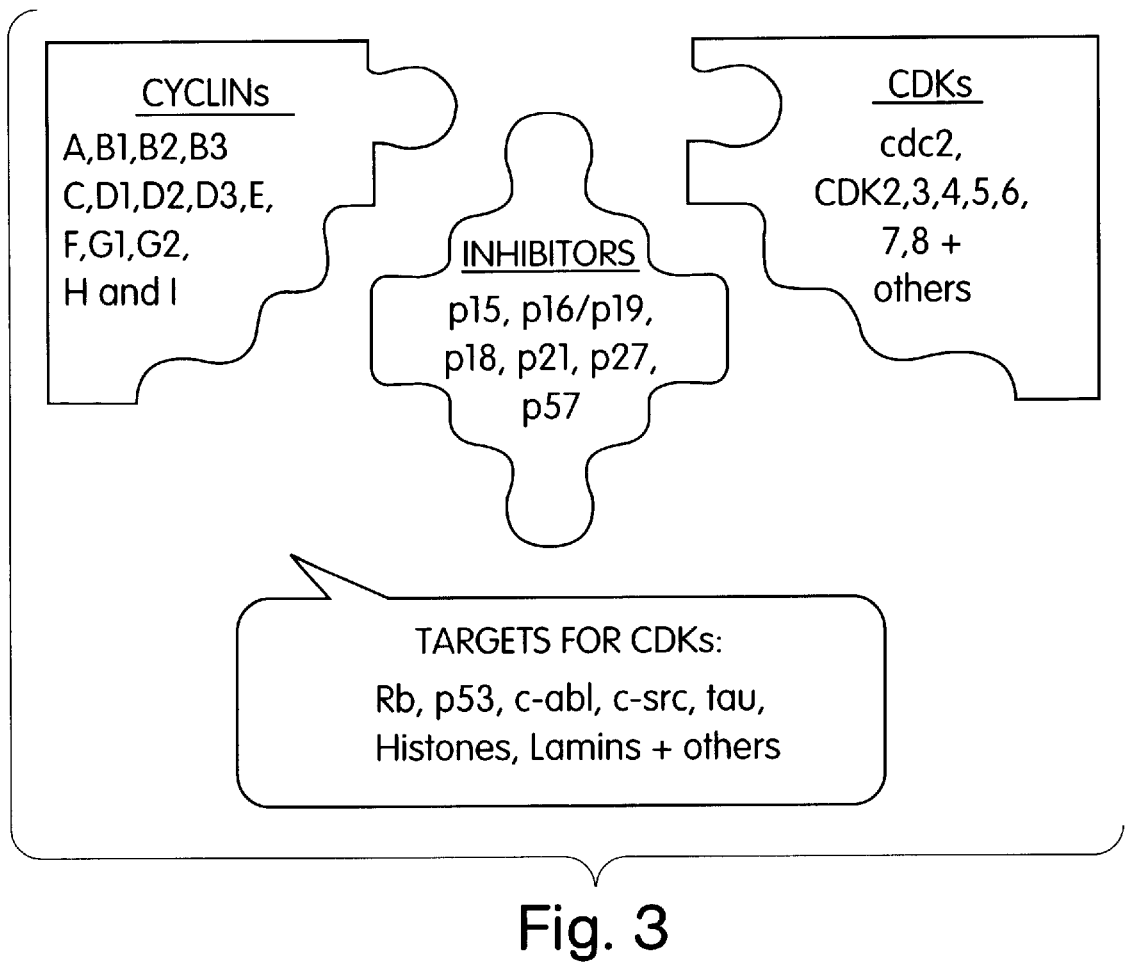
FIG. 3 is a schematic illustrating interactions between various controlling and inhibiting elements.

Events central to growth and development such as cell division, differentiation and quiescence are under tight regulation (FIG. 2). Cyclins and cyclin-dependent kinases form complexes that are able to phospho-regulate a wide variety of substrates involved in the orderly progression through the mitotic cycle (FIG. 3). Cells receiving external growth stimulus upregulate cyclin-dependent kinases and their cognate activating cyclins to orchestrate DNA replication, cytoskeletal re-organization and cellular metabolism required for proliferation. Whereas progression through the cell division cycle is controlled in part by the sequential synthesis and degradation of cyclins, growth arrest or terminal differentiation are controlled initially by cyclin-dependent kinase inhibitors, including p16, p21, p27 and p57 which, among other functions, directly inhibit the cyclin-CDK complex (FIG. 3). As depicted in FIG. 2, transition from the G1 phase of the cell cycle and commitment to S phase/DNA replication is thought to be mediated by the association of G1 cyclin/CDK complexes such as CDK2/cyclin E and CDK4/D-type cyclins. Phosphorylation of the retinoblastoma protein by CDK4/cyclinD, for example, enables release of E2F transcription factor and expression of genes required for DNA replication and proliferation. Active CDK complexes are negatively regulated by the competitive binding of tumor suppressor gene products such as p16, which disrupt the complex and indirectly inhibit E2F mediated gene expression.

The present invention contemplates detecting cell cycle-related proteins that are upregulated (as a result of re-entry into the cell cycle) as well as their relationship, both temporal and spatial, to more established markers of the disease. The present invention provides a means for detecting cell cycle abnormalities in the neuronal death that are characteristic of Alzheimer disease.

Neurons normally develop to exit from the mitotic cell cycle and enter into a quiescent state equivalent to G0. In Alzheimer disease, however, neurons express markers common to cells in a variety of stages of the cell cycle.

Using the transfected primary neurons discussed above, alterations in cytoskeletal phosphorylation has been detected that is akin to that found in neurons in Alzheimer disease. Detection is readily performed using immunocytochemical and immunoblotting analysis of cell cycle markers. In this regard, it is helpful to group markers grouped according to cell cycle position. For example, progression from G0 (Cyclin D, Cyclin E, Cyclin A, PCNA, Rb phosphorylation, E2f); progression into G2 (Cyclin B); exit from mitosis (p16, p14-arf, p19, p21, p27, p57). The spatio-temporal distribution and expression of these cell cycle antigens can also be correlated with that of other known markers of disease such as oxidative, mitochondrial, apoptotic, and cytoskeletal abnormalities.

D. Drug Screening Assay Systems

The screening assays are contemplated as utilizing various neuronal cells. In one embodiment, the present invention contemplates primary neurons that have been transfected (transiently or stably) with an expression vector comprising a combination of oncogenes. Importantly, the use of potential agonists or antagonists in these assay systems should allow for the detection of new compounds (e.g., drugs) which overcome or inhibit deleterious cell-cycle-related events.

The in vitro system permits the screening of many compounds. Importantly, the method is amenable to automation, providing the benefits of high throughput and reducing the amount of personnel time necessary to perform the assay.

Experimental

The following examples are provided in order to demonstrate and further illustrate certain aspects of the present invention. The examples are not to be construed as limiting the invention.

In some of the experiments described below, immunocytochemistry is performed. In some cases comparisons are made with brain tissue from diseased individuals. The methods involve obtaining tissue, fixation and staining.

Tissue: Brain tissue is obtained at autopsy from clinically and pathologically confirmed cases of AD by using NIA and CERAD criteria) and compared with tissue from non-demented control cases with similar postmortem intervals prior to fixation.

Fixation: Tissues are fixed in methacarn (methanol: chloroform: acetic acid, 6:3:1) or formalin for 16 hr at 4° C., dehydrated through graded ethanol followed by xylene, and embedded in paraffin. Six-micron thick sections are cut and mounted on Silane (Sigma, St. Louis)-coated standard glass microscope slides for in situ hybridization and immunocytochemical use.

Immunocytochemistry: Immunostaining is performed using the peroxidase-antiperoxidase procedure. After deparaffinization in xylene and rehydration through graded ethanol, endogeneous peroxidase activity is inhibited by 20 min incubation in 3% $H_2O_2$ and nonspecific protein binding sites are blocked with 10% normal goat serum in Tris-buffered saline (150 mM Tris-HCl, 10 mM NaCl, pH 7.6).

Immunostaining is readily achieved by the peroxidase-antiperoxidase technique using 3,3'-diaminobenzidine as chromogen. Adjacent sections are immunostained with a variety of antibodies (e.g. available from commercial sources such as UBI, Oncogene Science, Santa Cruz, Calif.) to confirm either the identity and location of pathological structures or the presence of various disease parameters. In certain cases, double stain experiments are used where the second antigen is localized with the alkaline phosphatase technique with fast blue as substrate. Alternatively, sequential stains are used where a soluble chromogen is employed.

Adsorption experiments can be performed to confirm the specificity of antibody binding. The immunostaining protocol is repeated, except here using adsorbed antiserum in parallel. Adsorbed antisera can be generated by incubation of primary antisera with purified protein diluted to a final concentration of 1–100 (g/ml for 3 hr at 37° C. Adsorption of anti-tau antibody can be performed as a control against artifactual absorption.

EXAMPLE 1

Figure 5:
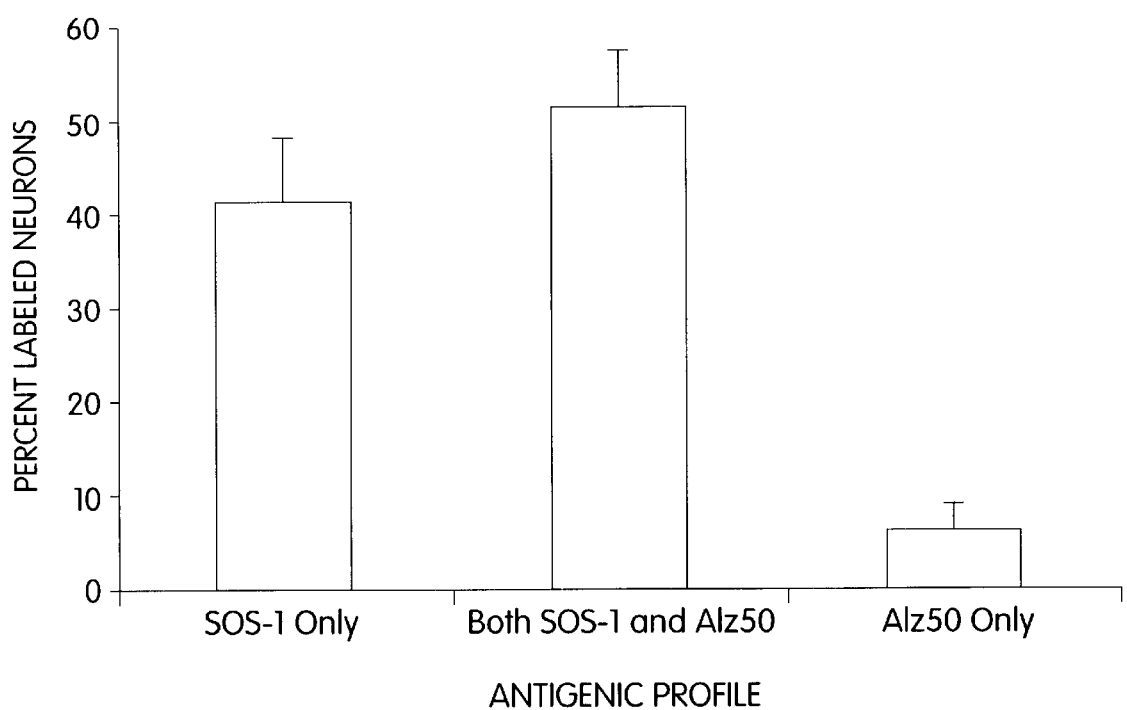
FIG. 5 is a bar graph showing the immunostaining Alzheimer neurons with antibody directed to SOS-1 and Alz50.

In this example, components known to trigger cellular proliferation and differentiation, upstream of the ras/mitogen-activated kinase pathway, were investigated. FIG. 5 shows the quantitative double immunolabeling results with both SOS-1 and Alz50 in Alzheimer neurons. Three cases showed that the vast majority of neurons labeled with both antisera or with SOS-1 exclusively, indicating that SOS-1 is functionally significant in the disease process.

EXAMPLE 2

The present invention contemplates the transfection of neuronal cells, thereby treating the cells so that they exhibit characteristics associated with the re-entry into the cell cycle. The present example describes one embodiment of a construct comprising oncogenes and subsequent transfection of primary neurons.

Design Of The Construct. C. Farnsworth and L. Reig describe the creation of constructs comprising a coding sequence of a ras oncogene. See C. Farnsworth and L. Reig, Mol. Cell. Biol. 11: 4822 (1991). Briefly, the gene described by those authors comprised the 5' end of viral $ras^H$ which was converted to the coding sequence of cellular $ras^H$ by site-directed mutagenesis, and the 3' end of a cellular ras cDNA clone. An approximately 900 bp HindlII-BamHI fragment of the ras gene was excised from M13 double-stranded DNA and inserted in place of the comparable fragment removed from the bacterial expression vector pXCR. The 0.7-kb Bg/II-BamHI fragment of pXCR was subcloned into the BamHI site of the mammalian expression vector pZIPneoSV(X).

For the present experiment, Ad-$Ras^{N17}$ was constructed by ligation of the HindiII/XbaI fragment from pRsαRas$^{N17}$ of Fransworth and Reig and the BamH1 fragment from pZIP-NeoSV(x) into the similarly digested pGEM-CMV vector. Ad-Myc was constructed by ligation of the HingIII/XbaI fragment from CMV-Myc containing the mouse c-myc cDNA into similarly digested pGEM-CMV vector. Viral stocks were created and virus was purified. Viral titres are determined by an indirect immunofluorescent assay specific for the viral 72K E2 gene product and defined as focus forming units (FFU) per ml.

Transfection of Primary Neurons. Primary neurons are prepared according to standard laboratory protocol. Briefly, newborn mice are decapitated and the brain removed. The meninges are removed and the tissue minced followed by dissociation of the cells in 0.05% trypsin (Type III, Sigma Chemical, St. Louis) at 37° C. for 20 minutes. The cell suspension is triturated in 4 Kunitz unit/ml DNase I and then plated on poly-L-lysine coated Falcon flasks. Shaking the flask 4–6 hours after plating at which time only the astrocytes are strongly adherent can isolate astrocytes. Neurons can be isolated by gently shaking 4–6 hours after plating the cortical cultures which detaches the neurons from the flask. The neurons are recovered in the media and replated on poly-L-lysine coated plates. Finally, microglial cells can be isolated by shaking cortical cultures on an orbital shaker 10 days after plating at 180 rpm for 1 hour after which they are plated on poly-L-lysine coated plates for one hour and the media containing other cell types is removed. The cell cultures can be assessed for purity using standard immunological techniques. The next day, the cells are washed once with D-MEM and the culture medium replaced with D-MEM containing 0.25% serum and cells further incubated for 48 h before virus infection. Cells on plates are infected in D-MEM with 20 mM HEPES, pH 7.2, for 75 min at 37° C. at a cell-to-volume ratio of $0.5 \times 10^6$ ml$^{-1}$. After infection, four volumes of 0.25% serum/D-MEM are added to each plate and the cells incubated at 37° C.

EXAMPLE 3

This example describes the changes detectable after the transfection of cells according to the procedures describe above in Example 1. Having adapted the adenovirus vector delivery system to induce high level expression of a constitutively active form of ras and wild-type c-myc into primary hippocampal neurons, the neurons were cultured and stained. The results showed that the neurons persist in culture with an enlarged cell body and are immunopositive for phospho-tau (immunolabeled with AT8). The results indicate that phosphorylated tau epitopes are increased in primary neuronal cultures transfected with Ras/Myc in comparison to those transfected with ras or Myc alone or non-transfected/mock transfected controls (cells were fixed 24 hours post-transfection).

From the above descriptions and examples, it should be clear that the methods and reagents of the present invention represent an easy, reliable method to determine the safety and efficacy of new compounds for the treatment of Alzheimer disease.

What is claimed is:

1. A screening method for testing compounds for their ability to inhibit a deleterious event associated with re-entry into the cell cycle comprising:
   a) providing, in any order:
      i) a reaction vessel;
      ii) a plurality of mammalian neuronal cells transfected with two oncogenes such that said transfected cells exhibit said deleterious event associated with reentry into the cell cycle, wherein said oncogenes are Myc and Ras; and
      iii) a test compound;
   b) combining said transfected cells and said test compound within said reaction vessel under conditions such that said compound is free to interact with said transfected cells;
   c) detecting said interaction under conditions such that the amount of inhibition of said deleterious event associated with re-entry into the cell cycle is measured; and
   d) determining the viability of said cells after contact with said test compound.

2. The method of claim 1, wherein said deleterious event is selected from the group consisting of phosphorylation of the tau protein, incorporation of a nucleic acid precursors into neuronal cell genes, increased expression of cyclin-dependent kinases, and increased expression of cyclin-dependent kinase inhibitors.

3. The method of claim 1, wherein said neuronal cells are primary neuronal cells.

4. A screening method for testing compounds for their ability to inhibit the phosphorylation of the tau protein comprising:
   a) providing, in any order:
      i) a reaction vessel;
      ii) a plurality of mammalian neuronal cells transfected with two oncogenes such that said transfected cells exhibit phosphorylation of the tau protein, wherein said oncogenes are Myc and Ras; and
      iii) a test compound;
   b) combining said transfected cells and said test compound within said reaction vessel under conditions such that said compound is free to interact with said transfected cells; and
   c) detecting said interaction under conditions such that the amount of inhibition of said phosphorylation is measured.

5. The method of claim 4, wherein said neuronal cells are primary neuronal cells.

6. The method of claim 4, wherein said amount of inhibition is measured using an anti-tau antibody.

* * * * *

SEQUENCE LISTING

<160> NUMBER OF SEQ ID NOS: 2

<210> SEQ ID NO 1
<211> LENGTH: 567
<212> TYPE: DNA
<213> ORGANISM: Homo sapiens

<400> SEQUENCE: 1

```
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttctttgt     240
gtatttgcca taaataatac taaatcattt gaagatattc accattatag agaacaaatt     300
aaaagagtta aggactctga agatgtacct atggtcctag taggaaataa atgtgatttg     360
ccttctagaa cagtagacac aaaacaggct caggacttag caagaagtta tggaattcct     420
tttattgaaa catcagcaaa gacaagacag ggtgttgatg atgccttcta tacattagtt     480
cgagaaattc gaaaacataa agaaaagatg agcaaagatg gtaaaaagaa gaaaaagaag     540
tgaaagacaa agtgtgtaat tatgtaa                                         567
```

<210> SEQ ID NO 2
<211> LENGTH: 567
<212> TYPE: DNA
<213> ORGANISM: Homo sapiens

<400> SEQUENCE: 2

```
atgactgaat ataaacttgt ggtagttgga gctgttggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttctttgt     240
gtatttgcca taaataatac taaatcattt gaagatattc accattatag agaacaaatt     300
```

-continued

```
aaaagagtta aggactctga agatgtacct atggtcctag taggaaataa atgtgatttg    360
ccttccagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaaagatg gtaaaaagaa gaaaaagaag    540
tgaaagacaa agtgtgtaat tatgtaa                                        567
```